United States Patent [19]

Ferrone

[11] Patent Number: 5,780,029

[45] Date of Patent: *Jul. 14, 1998

[54] ANTIDIOTYPIC MONOCLONAL ANTIBODIES FOR TREATMENT OF MELANOMA

[75] Inventor: Soldano Ferrone, Scarsdale, N.Y.

[73] Assignee: New York Medical College, Valhalla, N.Y.

[*] Notice: The term of this patent shall not extend beyond the expiration date of Pat. No. 5,493,009.

[21] Appl. No.: 549,423

[22] Filed: Oct. 27, 1995

Related U.S. Application Data

[62] Division of Ser. No. 41,885, Apr. 2, 1993, Pat. No. 5,493,009, which is a continuation of Ser. No. 595,064, Nov. 21, 1990, abandoned, which is a continuation of Ser. No. 435,885, Nov. 14, 1989, abandoned.

[51] Int. Cl.$^6$ .................. A61K 39/395; C07K 16/00; C12N 5/00
[52] U.S. Cl. ............................... 424/131.1; 424/138.1; 424/141.1; 424/155.1; 424/178.1; 435/327; 435/330; 530/387.2; 530/387.7
[58] Field of Search ............... 424/131.1, 138.1, 424/141.1, 155.1, 178.1, 174.1; 530/387.2, 387.7; 435/327, 330

[56] References Cited

PUBLICATIONS

Jurincic et al. J. Urol. 139(4) 723–6, 1988.
Herr, Uremia Invest. 8:257–61 (1985).
Kusama et al. Cancer Res. 47:4312–17, 15 Aug. 1987.
Giacomini et al. J. Immunol. 135:696–702, 1985.

*Primary Examiner*—Paula K. Hutzell
*Assistant Examiner*—Susan Ungar
*Attorney, Agent, or Firm*—Mathews, Collins, Shepherd & Gould, P.A.

[57] ABSTRACT

The invention concerns murine antiidiotypic monoclonal antibodies which are the internal image of determinants recognized by a monoclonal antibody on high molecular weight-melanoma associated antigen (HMW-MAA), antibody derivatives, hybridoma cell lines secreting such antiidiotypic monoclonal antibodies, and processes for the preparation of such antiidiotypic monoclonal antibodies, of their derivatives and of the hybridoma cell lines. The murine antiidiotypic monoclonal antibodies are useful for the determination of antibodies directed against high molecular weight-melanoma associated antigen, for the modulation of the immune response to HMW-MAA and for the treatment of melanoma.

6 Claims, 1 Drawing Sheet

ANTIDIOTYPIC MONOCLONAL ANTIBODIES FOR TREATMENT OF MELANOMA

This is a division of Ser. No. 08/041,885, filed Apr. 2, 1993, now U.S. Pat. No. 5,493,009, which is a continuation of Ser. No. 07/595,064, filed Nov. 21, 1990, now abandoned, which is a continuation of Ser. No. 07/435,885, filed Nov. 14, 1989, also abandoned.

The invention concerns murine antiidiotypic monoclonal antibodies which are the internal image of determinants recognized by a monoclonal antibody on high molecular weight-melanoma associated antigen (HMW-MAA), antibody derivatives, hybridoma cell lines secreting such antiidiotypic monoclonal antibodies, and processes for the preparation of such antiidiotypic monoclonal antibodies, of their derivatives and of the hybridoma cell lines. The murine antiidiotypic monoclonal antibodies are useful for the determination of antibodies directed against high molecular weight-melanoma associated antigen, for the modulation of the immune response to HMW-MAA and for the treatment of melanoma.

BACKGROUND OF THE INVENTION

Melanomas are tumors of the skin, less frequently of mucous membranes, some of which are benign. Malignant melanomas are carcinomas of neuroectodermal origin generally derived from melanocytes (pigment-producing cells), sometimes from mucous membranes, the chorioid coat or the meninges. There are several types of malignant melanoma which differ in localization, way of spreading and production of metastases.

Conventional treatment of melanoma includes surgery, radio- or chemotherapy, and the application of biological response modifiers. However, these methods have proved to be insufficient to combat the illness, e.g. to prevent tumor recurrence, and are complicated by a large number of severe side effects. Therefore, it is desirable to develop therapeutic approaches which overcome these drawbacks and can replace or be used in combination with conventional treatment.

Since the immune system seems to be heavily involved in the pathogenesis of this disease, the most suitable treatment would be a method of active immunotherapy, for example based on the application of specific antiidiotypic antibodies. Antiidiotypic antibodies are directed against particular antibody idiotypes (full set of antibody variable region determinants), and are produced by using antibodies as immunogens. Antiidiotypic antibodies are therefore often designated as Ab 2 (antibody 2) while the immunizing antibody is referred to as Ab 1 (antibody 1). In recent years, it has been shown that antiidiotypic antibodies raised against antibodies to a variety of antigens are useful reagents to manipulate the immune response to the corresponding antigens, presumably by balancing amplification and suppressor signals among immune cell subsets. Of special interest for therapeutic application are antiidiotypic antibodies of the internal image type which mimic the initial antigen and can substitute for it. For tumor therapy, suitable antiidiotypic antibodies are those which are raised against antibodies specific for tumor associated antigens. In melanoma, suitable targets for the production of antiidiotypic antibodies and the development of immunotherapeutic approaches are the melanoma associated antigens (MAA), a number of which have been identified and characterized by their molecular weight, for example high molecular weight-melanoma associated antigen (HMW-MAA) with a molecular weight of >1,000,000.

OBJECT OF THE INVENTION

It is an object of this invention to provide murine antiidiotypic monoclonal antibodies (MAbs) which are the internal image of determinants recognized by monoclonal antibodies on high molecular weight-melanoma associated antigen (HMW-MAA). Such antiidiotypic MAbs can be produced by using monoclonal antibodies, e.g. syngeneic monoclonal antibodies, directed against HMW-MAA for immunization. The choice of the immunizing antibody determines which epitopes of HMW-MAA are mimicked by the antiidiotypic antibodies.

The antiidiotypic monoclonal antibodies of the invention have immune-regulatory functions such as the stimulation of humoral and cellular immunity. Consequently, the antiidiotpyic monoclonal antibodies of the invention can be used for many diagnostic and therapeutic purposes, e.g. for control, prevention, treatment and monitoring of melanoma.

DESCRIPTION OF THE INVENTION

The invention concerns murine antiidiotypic monoclonal antibodies which are the internal image of determinants recognized by a monoclonal antibody on human high molecular weight-melanoma associated antigen (HMW-MAA), and derivatives thereof which retain the specificity of the antibody from which they are derived.

Antiidiotypic antibodies (Ab 2) are directed against the variable region of another antibody molecule (Ab 1), i.e. against particular antibody idiotypes (full set of antibody variable region determinants). Internal image antiidiotypic antibodies are reactive with antigen-binding structures on the immunizing antibody which are complementary to the antigen, i.e. such antibodies represent the conformational mirror image of the antigen and can be used as its substitute. Internal image antibodies in vitro inhibit the binding of the immunizing antibody to target cells, and elicit in vivo anti-antiidiotypic antibodies, also designated as Ab 3 (antibody 3), which are directed against the antigen and have the same reactivity pattern as Ab 1.

In the present invention, the murine antiidiotypic monoclonal antibodies, which are produced against anti-HMW-MAA monoclonal antibodies as described in detail hereinbelow, mimic determinants of HMW-MAA recognized by the immunizing antibodies. They recognize idiotopes within the antigen combining site of the immunizing anti-HMW-MAA monoclonal antibody Ab I and therefore inhibit the binding of Ab 1 to melanoma cells expressing HMW-MAA, and induce anti-antiidiotypic antibodies (Ab 3) reactive with HMW-MAA. The specificity of the antiidiotypic monoclonal antibodies according to the invention for the immunizing anti-HMW-MAA monoclonal antibody is tested in an immunoassay, for instance a binding assay in which carriers are coated with Ab 1, incubated with labelled, e.g. radioactively or enzyme-labelled, antiidiotypic monoclonal antibodies of the invention, and the bound label is detected. To investigate whether the murine antiidiotypic monoclonal antibodies recognize idiotopes within the antigen combining site of the monoclonal antibody used for immunization, their ability to inhibit the binding of Ab 1 to melanoma cells expressing HMW-MAA is tested, for example in an immunoassay. Such an immunoassay may be a competitive radio- or enzyme immunoassay where the labelled, e.g. radioactively or enzyme-labelled, immunizing anti-HMW-MAA monoclonal antibody is incubated with a corresponding antiidiotypic monoclonal antibody of the invention, the mixture is added to HMW-MAA carrying melanoma cells, e.g. cultured melanoma cells Colo 38, and the bound label is measured after further incubation. To determine that the antiidiotypic monoclonal antibodies of the invention are of the internal image type, it is examined whether they are capable of inducing anti-antiidiotypic antibodies which are reactive with HMW-MAA and exhibit the same reactivity pattern as Ab 1. The induction of anti-antiidiotypic antibodies can be performed in an animal model, for example in mice. The generated anti-antiidiotypic antibodies are for instance tested for their specificity for HMW-MAA, e.g. in an immunoassay investigating their binding to HMW-MAA carrying melanoma cells, and electrophoretic analysis, for example sodium dodecylsulphate-polyacrylamide gel electrophoresis (SDS-PAGE), of the antigens immunoprecipitated from the cells. The anti-antiidiotypic antibodies can also be tested for their reactivity with the antiidiotypic antibody used for generation.

High molecular weight-melanoma associated antigen (molecular weight >1,000,000) is chosen as a target for the production of antiidiotypic antibodies since HMW-MAA meets most, if not all, in vitro criteria for the development of immunotherapeutic approaches in treatment of melanoma, as indicated by the characteristics shown in Table 1 below.

TABLE 1

Characteristics of the HMW-MAA

| | |
|---|---|
| Cell distribution: | membrane bound |
| Frequency in surgically removed melanoma lesions: | high (at least 85% of lesions tested) |
| Distribution in normal tissues: | restricted (only basal cells of epidermis and hair follicles) |
| Level in serum: | low |
| Susceptibility to modulation by antibodies and lymphokines: | low |
| Density on tumor cells: | high (between $1 \times 10^5$ and $2 \times 10^6$ antigenic sites/cultured melanoma cell) |

The murine antiidiotypic monoclonal antibodies of the invention may be of any immunoglobulin class/subclass, preferentially of immunoglobulin class IgG, in particular of immunoglobulin subclass IgG1. Since different isotypes of antiidiotypic antibodies may have different immune-regulatory action, the antiidiotypic MAbs can be chosen accordingly.

In particular, the invention concerns murine antiidiotypic monoclonal antibodies which are the internal image of determinants of HMW-MAA recognized by the monoclonal antibody designated MAb 763.74 and derivatives thereof. The monoclonal antibody MAb 763.74 is described by P. Giacomini et al. (J. Immunol. 135, 696, 1985).

Especially preferred is the murine antiidiotypic monoclonal antibody designated MAb MK2-23, and derivatives thereof. This antiidiotypic MAb is raised against MAb 763.74 and is the internal image of determinants of HMW-MAA recognized by MAb 763.74. MAb MK2-23 is capable of eliciting antibodies which mimic the characteristics of MAb 763.74. The MK2-23 hybridoma cell line was deposited on Oct. 31, 1989 with the American Type Culture Collection (ATCC) under the terms of the Budapest Treaty, under Accession No. HB 10288.

Derivatives of an antiidiotypic monoclonal antibody of the invention retain the specificity of the antibody from which they are derived, i.e. they retain the characteristic binding pattern of the parent antibody. Examples of such derivatives are antiidiotypic monoclonal antibody fragments, conjugates of the antiidiotypic monoclonal antibodies with a carrier which enhances the immunogenicity, with an enzyme, with a fluorescent marker, with a chemiluminescent marker, with a metal chelate, with paramagnetic particles, with avidin, with biotin or the like, or radioactively labelled antiidiotypic monoclonal antibodies.

Antibody fragments of the invention are for example the univalent fragments Fab or Fab' or the divalent fragment $F(ab')_2$.

Suitable carrier molecules enhancing the immunogenicity of the antiidiotypic monoclonal antibodies of the invention are for example lysine rich proteins with free amino groups available for coupling, especially high molecular weight proteins like bovine serum albumin (BSA; MW 66,200), α-amylase from *Bacillus subtilis* (MW 58,000) or keyhole limpet haemocyanin (KLH; MW>1,000,000) which are commercially available in large quantities. Porcine thyroglobulin, toxins such as tetanus-, cholera- or diphteria-toxins, human serum albumin (HSA), β-2 microglobulin, and the like, may also be used as carriers. Other possible carrier molecules include polysaccharides, natural or synthetic lipopolysaccharides, synthetic polypeptides such as polylysins, activated membranes, latex particles, bacteria such as Salmonella, and the like.

Enzymes used for antibody conjugates of the invention are, for example, horseradish peroxidase, alkaline phosphatase, 5-D-galactosidase, glucose oxidase, glucoamylase, carbonic anhydrase, acetylcholinesterase, lysozyme, malate dehydrogenase or glucose-6-phosphate dehydrogenase.

Fluorescent markers conjugated with antibodies of the invention can be fluorescein, fluorochrome, rhodamine, and the like.

Chemiluminescent markers are e.g. acridinium derivatives such as acridinium esters of luminol.

Examples of metal chelates are ethylenediaminetetraacetic acid (EDTA), diethylenetriaminepentaacetic acid (DPTA), 1,4,8,11-tetraazatetradecane, 1,4,8,11-tetraazatetradecane-1,4,8,11-tetraacetic acid, 1-oxa-4,7,12,15-tetraazaheptadecane-4,7,12,15-tetraacetic acid, or the like.

In such conjugates, the antibody is bound to the conjugation partner directly or by way of a spacer or linker group.

Radioactively labelled antibodies of the invention contain e.g. radioactive iodine ($^{123}I$, $^{125}I$, $^{131}I$), tritium ($^3H$), carbon ($^{14}C$), sulfur ($^{35}S$), yttrium ($^{90}Y$), technetium ($^{99m}Tc$), or the like.

The murine antiidiotypic monoclonal antibodies of the invention and derivatives thereof are obtained by processes known per se wherein cells of a hybridoma cell line secreting the desired antiidiotypic monoclonal antibodies are multiplied in vitro or in vivo and, when required, the obtained antiidiotypic monoclonal antibodies are isolated and/or converted into derivatives thereof.

Multiplication in vitro is carried out in suitable culture media, which are the customary standard culture media, for example Dulbecco's Modified Eagle Medium (DMEM) or RPMI 1640 medium, optionally replenished by a mammalian serum, e.g. fetal calf serum, or trace elements and growth sustaining supplements, e.g feeder cells such as normal mouse peritoneal exudate cells, spleen cells, bone marrow macrophages, 2-aminoethanol, insulin, transferrin, low density lipoprotein, oleic acid, or the like.

In vitro production provides relatively pure antibody preparations and allows scale-up to give large amounts of the desired antibodies. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibres, microcapsules, on agarose microbeads or ceramic cartridges.

Large quantities of the desired antiidiotypic monoclonal antibodies can also be obtained by multiplying the cells in vivo. For this purpose, hybridoma cells producing the desired antibodies are injected into histocompatible mammals to cause growth of antibody-producing tumours. Optionally, the animals are primed with a hydrocarbon, especially mineral oils such as pristane (tetramethylpentadecane), prior to the injection. After one to three weeks, the antibodies are isolated from the body fluids of those mammals. For example, hybridoma cells derived from Balb/c mice that produce the desired monoclonal antibodies are injected intraperitoneally into Balb/c mice optionally pre-treated with pristane, and, after one to two weeks, ascitic fluid is taken from the animals.

Fragments of the antiidiotypic monoclonal antibodies, for example Fab, Fab' or F(ab')$_2$ fragments, can be obtained from the antiidiotypic antibodies prepared as described above by methods known per se, e.g. by digestion with enzymes such as papain or pepsin and/or cleavage of disulfide bonds by chemical reduction.

The antiidiotypic monoclonal antibody derivatives of the invention with enhanced immunogenicity are prepared by methods known per se, either by adsorption of the antiidiotypic monoclonal antibody to the carrier or by coupling using periodate, glutaraldehyde, carbodiimides e.g. N,N'-o-phenylenedimaleimide, N-(-m-maleimidobenzoyloxy)-succinimide, N-(3-[2'-pyridyldithio]-propionoxy)-succinimide, N-ethyl-N'-(3-dimethyl aminopropyl)-carbodiimide or the like.

Conjugates of antiidiotypic monoclonal antibodies of the invention with an enzyme, a fluorescent marker, a chemiluminescent marker, a metal chelate, paramagnetic particles, avidin, biotin or the like, are prepared by methods known in the art, e.g. by reacting an antibody prepared as described above in the presence of a coupling agent, e.g. gluturaldehyde, periodate, N,N'-o-phenylenedimaleimide, N-(m-maleimidobenzoyloxy)-succinimide, N-(3-[2'-pyridyldithio|-propionoxy)succinimide, N-ethyl-N'-(3-dimethylaminopropyl)-carbodiimide or the like. Conjugates with biotin are prepared e.g. by reacting antibodies with an activated ester of biotin such as the biotin N-hydroxysuccinimide ester. Conjugates with fluorescent or chemiluminescent markers are prepared in the presence of a coupling agent, e.g. those listed above, or by reaction with an isothiocyanate, preferably fluorescein-isothiocyanate.

Antiidiotypic monoclonal antibodies radioactively labelled with iodine ($^{123}$I, $^{125}$I, $^{131}$I) are obtained from the antibodies of the invention by iodination known per se, for example with radioactive sodium or potassium iodide and a chemical oxidizing agent, such as sodium hypochlorite, chloramine T or the like, or an enzymatic oxidizing agent, such as lactoperoxidase or glucose oxidase and glucose. Antibodies according to the invention are labelled with yttrium ($^{90}$Y) for example by diethylenetriaminepentaacetic acid (DPTA)-chelation. Technetium-99m labelled antibodies are prepared by ligand exchange processes, for example by reducing pertechnate (TcO$_4^-$) with stannous ion solution, chelating the reduced technetium onto a Sephadex column and applying the antibodies to this column, or by direct labelling techniques, e.g. by incubating pertechnate, a reducing agent such as SnCl$_2$, a buffer solution such as sodium potassium phthalate solution, and the antibodies.

The invention further concerns hybridoma cell lines which secrete the murine antiidiotypic monoclonal antibodies of the invention.

In particular, the invention concerns hybridoma cell lines which are hybrids of myeloma cells and B lymphocytes of a mouse immunized with a monoclonal antibody, preferentially a syngeneic monoclonal antibody, directed against high molecular weight-melanoma associated antigen. Preferentially, these cell lines are hybrids of mouse myeloma cells and B lymphocytes of a mouse, for example a Balb/c mouse, immunized with MAb 763.74. Especially preferred is the hybridoma cell line MK2-23 which has been deposited at the American Type Culture Collection (ATCC), 12301 Parklawn Drive, Rockville, Md. 20852, U.S.A., on Oct. 31, 1989, under the number HB 10288.

The hybridoma cell lines of the invention are genetically stable, secrete murine antiidiotypic monoclonal antibodies of the invention with constant specificity and may be kept in deep-frozen cultures and reactivated by thawing and optionally re-cloning.

The invention also concerns a process for the preparation of hybridoma cell lines secreting the murine antiidiotypic monoclonal antibodies of the invention wherein a mouse is immunized with a monoclonal antibody, preferentially a syngeneic monoclonal antibody, directed against high molecular weight-melanoma associated antigen or a conjugate thereof, antibody-producing cells of the mouse are fused with cells of a continuous cell line, the hybrid cells obtained in the fusion are cloned, and cell clones secreting the desired monoclonal antibodies are selected.

The immunogen used to elicit antiidiotypic monoclonal antibodies is a monoclonal antibody itself. Suitable immunizing antibodies for the production of the murine antiidiotypic MAbs of the invention are monoclonal antibodies, in particular syngeneic (homogeneous) monoclonal antibodies, which recognize idiotopes on high molecular weight-melanoma associated antigen. Suitable monoclonal antibodies can be of any immunoglobulin isotype. As explained above, the specificity of the monoclonal antibody used for immunization determines which determinants of high molecular weight-melanoma associated antigen are mimicked by the antiidiotypic MAbs and can therefore be chosen individually depending on the type of immune reaction which is to be influenced by application of the antiidiotypic monoclonal antibodies. A preferred immunogen is MAb 763.74 (P. Giacomini et al., loc. cit.).

The antigen, i.e. the immunizing monoclonal antibody, may be coupled to a carrier to enhance the immunogenicity of the monoclonal antibody. Suitable carrier molecules are for example lysine rich proteins with free amino groups available for coupling, especially high molecular weight proteins like bovine serum albumin (BSA; MW 66,200), α-amylase from Bacillus subtilis (MW 58,000) or keyhole limpet haemocyanin (KLH; MW>1,000,000) which are commercially available in large quantities. Porcine thyroglobulin, toxins such as tetanus-, cholera- or diphteria-toxins, human serum albumin (HSA), β-2 microglobulin, and the like, may also be used as carriers. Other possible carrier molecules include polysaccharides, natural or synthetic lipopolysaccharides, synthetic polypeptides such as polylysins, activated membranes, latex particles, bacteria such as Salmonella, and the like.

The immunogenic conjugates of the invention are prepared by methods known per se, either by adsorption of the immunizing monoclonal antibody to the carrier or by coupling using periodate, glutaraldehyde, carbodiimides e.g. N,N'-o-phenylenedimaleimide, N-(-m-maleimidobenzoyloxy)-succinimide, N-(3-|2'-pyridyldithio|-propionoxy)-succinimide, N-ethyl-N'-(3-dimethyl aminopropyl)-carbodiimide or the like.

Preferred is a conjugate of the immunizing monoclonal antibody in which the immunizing MAb is coupled to keyhole limpet haemocyanin (KLH) with glutaraldehyde.

The immunogen may be mixed with adjuvants, i.e. agents which will further increase the immune response, for the immunization procedure. Possible adjuvants are Freund's complete adjuvant (emulsion of mineral oil, water, and mycobacterial extracts), Freund's incomplete adjuvant (emulsion of water and oil only), mineral gels, e.g. aluminium hydroxide gels, surface active substances such as lysolecithin, polyanions, peptides, BCG (Bacillus Calmette-Guerin), etc.

The routes of immunization include, among others, intradermal, subcutaneous, intramuscular, intraperitoneal, intravascular and intracranial injections. Since high antibody titers are desired, a series of injections is commonly given. The immunization is for example performed by injecting the antigen two, three, four or more times parenterally, e.g. intraperitoneally and/or subcutaneously, in regular or irregular intervals of a few days, e.g. three to seven days, up to several months, for example four weeks.

Antibody-producing cells of the immunized mice, preferably lymphoid cells such as spleen lymphocytes, taken for example one to five days after the final injection, are fused with the cells of a continuous cell line, i.e. a continuously replicating cell clone which confers this replication ability to the hybrid cells resulting from the fusion. An example for such a cell line is a tumour cell line (myeloma) which does not itself actually produce immunoglobulins or fragments thereof but has the potential to produce and secrete large amounts of antibody, and which carries a genetic marker so that the hybrid cells can be selected against non-fused parent cells. Several suitable myeloma cell lines are known in the art. Preferred are myeloma cell lines lacking the enzyme hypoxanthine guanine phosphoribosyl transferase (HGPRT) or the enzyme thymidine kinase (TK), which therefore do not survive in a selective culture medium containing hypoxanthine, aminopterin and thymidine (HAT medium). Particularly preferred are myeloma cells and derived cell lines that do not survive in HAT medium and do not secrete immunoglubulins or fragments thereof, such as the cell lines P3x63Ag8.653 or Sp2/0-Ag14.

The fusion is performed in the presence of a fusion promoter, for example Sendai virus or other paramyxo viruses, optionally in UV-inactivated form, or chemical fusogens such as calcium ions, surface-active lipids, e.g. lysolecithin, or polyethylene glycol (PEG), or by electrofusion. Preferentially, the myeloma cells are fused with a three- to twentyfold excess of spleen cells from immunized mammals in a solution containing about 30% to about 60% of polyethylene glycol of a molecular weight between 1000 and 4000.

After the fusion, the cells are resuspended and cultivated in a selective medium chosen depending on the genetic selection marker, for example HAT medium. In this medium, only hybridoma cells will survive, because they combine the ability to grow and replicate in vitro inherited from the parent myeloma cells and the missing HGPRT or TK genes essential for the survival in HAT medium inherited from the antibody-producing spleen cells of the immunized mammals.

Suitable culture media for the expansion of hybridoma cells are the standard culture media, such as Dulbecco's Modified Eagle Medium (DMEM), minimum essential medium, RPMI 1640 and the like, optionally replenished by a mammalian serum, e.g. 10 to 15% fetal calf serum. Preferentially, feeder cells, e.g. normal mouse peritoneal exudate cells, spleen cells, bone marrow macrophages or the like, are added at the beginning of cell growth immediately after the fusion step to nourish the hybridoma cells and support their growth, especially where cell densities are low, by providing growth factors and the like. If phagocytic cells such as macrophages or monocytes are used, they can perform a helpful service in cleaning up the debris of dead myeloma cells always found after aminopterin treatment. The culture media are supplemented with selective medium in order to prevent myeloma cells from overgrowing the hybridoma cells.

The hybridoma cell culture supernatants are screened for the desired murine antiidiotypic monoclonal antibodies with an immunoassay, preferentially with a radio- or enzyme immunoassay. Such an immunoassay is for example an indirect binding assay wherein a carrier is coated with the immunizing monoclonal antibody or a fragment thereof, hybridoma supernatants are added and the antiidiotypic monoclonal antibodies bound to the carrier are detected by addition of labelled antibodies which recognize the antiidiotypic antibodies.

Positive hybridoma cells are cloned, e.g. by limiting dilution or in soft agar, preferentially twice or more. Optionally, hybridoma cells are passaged through animals, e.g. mice, by intraperitoneal injection and harvesting of ascites, which stabilizes hybridomas and improves growth characteristics. The cloned cell lines may be frozen in a conventional manner.

The murine antiidiotypic monoclonal antibodies and their derivatives according to the invention are useful for a number of therapeutic and diagnostic purposes. The advantages of using internal-image antiidiotypic monoclonal antibodies instead of the HMW-MAA itself are for instance:

higher immunogenicity of the antiidiotypic MAbs, stimulation of B-cell clones normally unresponsive to HMW-MAA by the antiidiotypic MAbs, possible generation of anti-HMW-MAA cytotoxic T-cells, which are not HLA class I restricted, by the antiidiotypic MAbs, elimination of side effects which might be associated with the application of HMW-MAA, easy production of large amounts of antiidiotypic MAbs.

The murine antiidiotypic monoclonal antibodies and their derivatives according to the invention can for example be used to modulate the immune response to high molecular weight-melanoma associated antigen due to their immune-regulatory functions within the idiotype-antiidiotype reaction network. The modulation is specific and can be directed by the choice of the monoclonal antibody used for the production of the antiidiotypic MAbs, i.e. the specificity of the immunizing MAb, and by the isotype of the antiidiotypic MAbs, since different isotypes of antiidiotypic antibodies may have different immune-regulatory action.

Consequently, the murine antiidiotypic MAbs and derivatives thereof according to the invention are useful agents for the control and treatment of melanoma, that is to say that they can be successfully employed e.g. to cause tumor regression and/or prevent tumor recurrence. The antiidiotypic MAbs of the invention can be "tailor-made" to mimic specific determinants of HMW-MAA by the adequate choice of the immunizing antibody.

Moreover, the antiidiotypic MAbs of the invention are useful for preventing melanoma by induction of immunity against the determinants of high molecular weight-melanoma associated antigen recognized by the immunizing monoclonal antibody.

The invention also concerns pharmaceutical compositions comprising a murine antiidiotypic monoclonal antibody and/or a derivative thereof according to the invention. The pharmaceutical compositions comprise, for example, the murine antiidiotypic monoclonal antibodies and/or derivatives thereof in a therapeutically effective amount together or in admixture with inorganic or organic, solid or liquid carriers. Preferred are pharmaceutical compositions comprising a derivative of a murine antiidiotypic monoclonal of the invention which is a conjugate of an antiidiotypic monoclonal antibody with a carrier which enhances the immunogenicity, in particular with keyhole limpet haemocyanin (KLH). The pharmaceutical compositions of the invention may also comprise adjuvants, i.e. agents further increasing the immune response. Possible adjuvants are Freund's complete adjuvant (emulsion of mineral oil, water, and mycobacterial extracts), Freund's incomplete adjuvant (emulsion of water and oil only), mineral gels, e.g. aluminium hydroxide gels, surface active substances such as lysolecithin, polyanions, peptides, BCG (Bacillus Calmette-Guerin), etc. Particularly preferred are pharmaceutical compositions comprising a conjugate of an antiidiotypic monoclonal antibody with a carrier which enhances the immunogenicity and an adjuvant, preferentially an antiidiotypic monoclonal antibody coupled to keyhole limpet haemocyanin (KLH) and Bacillus Calmette-Guerin (BCG).

Preferred are pharmaceutical compositions for parenteral application. Compositions for intramuscular, subcutaneous or intravenous application are e.g. isotonic aqueous solutions or suspensions, optionally prepared shortly before use from lyophilized or concentrated preparations. The pharmaceutical compositions may be sterilized and contain adjuvants e.g. for conserving, stabilizing, wetting, emulsifying or solubilizing the ingredients, salts for the regulation of the osmotic pressure, buffer and/or compounds regulating the viscosity, e.g. sodium carboxycellulose, dextran, polyvinylpyrrolidine or gelatine. They are prepared by methods known in the art, e.g. by conventional mixing, dissolving or lyophilizing, and contain from approximately 0.01% to approximately 50% of active ingredients. The compositions for injections are processed, filled into ampoules or vials, and sealed under aseptic conditions according to methods known in the art.

The specific mode of administration and the dosage will be selected by the attending physician taking into account the particulars of the patient, the state of the disease, the type of melanoma treated, and the like. The therapeutic dose for mammals is between approximately 30 µg and 100 µg per kg body weight depending on the status of the patient and the mode of application.

For example, in a study with ten patients suffering advanced melanoma, the application of the murine antiidiotypic monoclonal antibody MAb MK2-23 according to the invention results in complete remission in one patient and in partial remission in another patient.

The murine antiidiotypic MAbs and derivatives thereof according to the invention can also be used for the qualitative and quantitative determination of antibodies directed against high molecular weight-melanoma associated antigen. This is especially useful for the monitoring of the treatment of melanoma with the murine antiidiotypic MAbs and derivatives thereof.

For instance, the murine antiidiotypic monoclonal antibodies or derivatives thereof according to the invention can be used in any of the known immunoassays which rely on the binding interaction between the idiotopes of the antibodies directed against HMW-MAA and of the antiidiotypic monoclonal antibodies. Examples of such assays are radio-, enzyme, fluorescence, chemiluminescence, immunoprecipitation, latex agglutination, and hemagglutination immunoassays.

The murine antiidiotypic monoclonal antibodies according to the invention can be used as such or in the form of radioactively labelled derivatives in a radioimmunoassay (RIA). Any of the known modifications of a RIA can be used, for example soluble phase (homogeneous) RIA, solid phase (heterogeneous) RIA, single RIA or double (sandwich) RIA with direct or indirect (competitive) determination of antibodies directed against high molecular weight-melanoma associated antigen.

An example of such a radioimmunoassay is a sandwich RIA in which a suitable carrier, for example the plastic surface of a microtiter plate or of a test tube, e.g. of polystyrene, polypropylene or polyvinylchloride, glass or plastic beads, filter paper, dextran etc. cellulose acetate or nitrocellulose sheets, magnetic particles or the like, is coated with a murine antiidiotypic monoclonal antibody of the invention by simple adsorption or optionally after activation of the carrier, for example with glutaraldehyde or cyanogen bromide. Then test solutions containing antibodies directed against HMW-MAA and finally polyclonal antibodies which also react with the anti-MAA antibodies and which are radioactively labelled, e.g. with $^{125}$I, are added. The amount of antibodies directed against high molecular weight-melanoma associated antigen in the test solution is directly proportional to the amount of bound polyclonal antibodies and is determined by measuring the radioactivity of the solid phase.

The murine antiidiotypic monoclonal antibodies according to the invention can be used as such or in the form of enzyme-conjugated derivatives in an enzyme immunoassay. As described above for radioimmunoassays, any of the known modifications of an enzyme immunoassay can be used.

The tests are carried out in an analogous manner to the radioimmunoassays described above using an enzyme label instead of a radioactive label. The amount of immune complex formed which corresponds to the amount of antibodies directed against HMW-MAA present in the test solutions is determined by adding an enzyme substrate solution. The enzyme substrate reaction results, for example, in a color change which can be observed by eye or with optical measuring devices.

The murine antiidiotypic monoclonal antibodies according to the invention can be used as such or in the form of derivatives conjugated with chemiluminescent markers in a chemiluminescence immunoassay. As described above for radioimmunoassays, any of the known modifications of a chemiluminescence immunoassay can be used.

The tests are carried out in an analogous manner to the radioimmunoassays described above using a chemiluminescent label instead of a radioactive label. The amount of immune complex formed which corresponds to the amount of antibodies directed against HMW-MAA present in the test solutions is determined by adding a compound triggering luminescence, e.g. $H_2O_2$ and NaOH, and measuring the emission of light with optical measuring devices.

The use according to the invention of antiidiotypic monoclonal antibodies and derivatives thereof as described hereinbefore for the determination of antibodies directed against high molecular weight-melanoma associated antigen also includes other immunoassays known per se, for example immunofluorescence assays, latex agglutination, hemagglutination, evanescent light assays using an optical fibre coated with an antiidiotypic MAb and other direct-acting immunosensors which convert the binding event into an electrical or optical signal, or the like.

The invention also concerns test kits for the qualitative and quantitative determination of antibodies directed against high molecular weight melanoma-associated antigen comprising murine antiidiotypic monoclonal antibodies of the invention and/or derivatives thereof and, optionally, other polyclonal or monoclonal antibodies and/or adjuncts.

Test kits according to the invention for a radioimmunoassay contain, for example, a suitable carrier, optionally freeze-dried solutions of one or more polyclonal and/or monoclonal antibodies, solutions of a radioactively labelled antibody, standard solutions of antibodies directed against HMW-MAA, buffer solutions, and, optionally, polypeptides or detergents for preventing non-specific adsorption and aggregate formation, pipettes, reaction vessels, calibration curves, instruction manuals and the like. One of the antibodies of the test kit is an antiidiotypic monoclonal antibody of the invention.

Test kits according to the invention for an enzyme immunoassay contain, for example, a suitable carrier, optionally freeze-dried solutions of one or more polyclonal and/or monoclonal antibodies, optionally freeze-dried or concentrated solutions of an enzyme- or biotin-conjugated antibody, solutions of an enzyme-avidin conjugate if biotin-labelled antibody is used, enzyme substrate in solid or dissolved form, standard solutions of antibodies directed against HMW-MAA, buffer solutions, and, optionally, polypeptides or detergents for preventing non-specific adsorption and aggregate formation, pipettes, reaction vessels, calibration curves, instruction manuals and the like. One of the antibodies of the test kit is an antiidiotypic monoclonal antibody of the invention.

The following examples illustrate the invention but do not limit it to any extent.
Abbreviations

| | |
|---|---|
| BCG | Bacillus Calmette-Guerin |
| CFA | complete Freund's adjuvant |
| DEAE | diethylaminoethyl |
| FCS | fetal calf serum |
| FPLC | fast protein liquid chromatography |
| HAT | hypoxanthine/aminopterin/thymidine |
| HLA | human lymphocyte antigens |
| HT | hypoxanthine/thymidine |
| ICAM-1 | anti intercellular adhesion molecule-1 |
| IFA | incomplete Freund's adjuvant |
| i.p. | intraperitoneal(ly) |
| KLH | keyhole limpet haemocyanin |
| PBS | phosphate buffered saline |
| PBS-T20 | phosphate buffered saline supplemented with 0.05% Tween 20 |
| RT | room temperature |
| SDS-PAGE | sodium dodecylsulphate-polyacrylamide gel electrophoresis |

circles: antiidiotypic MAb MK2-23 squares: antiidiotypic MAb MK2-72 triangles: antiidiotypic MAb MK2-120

Figure 2:
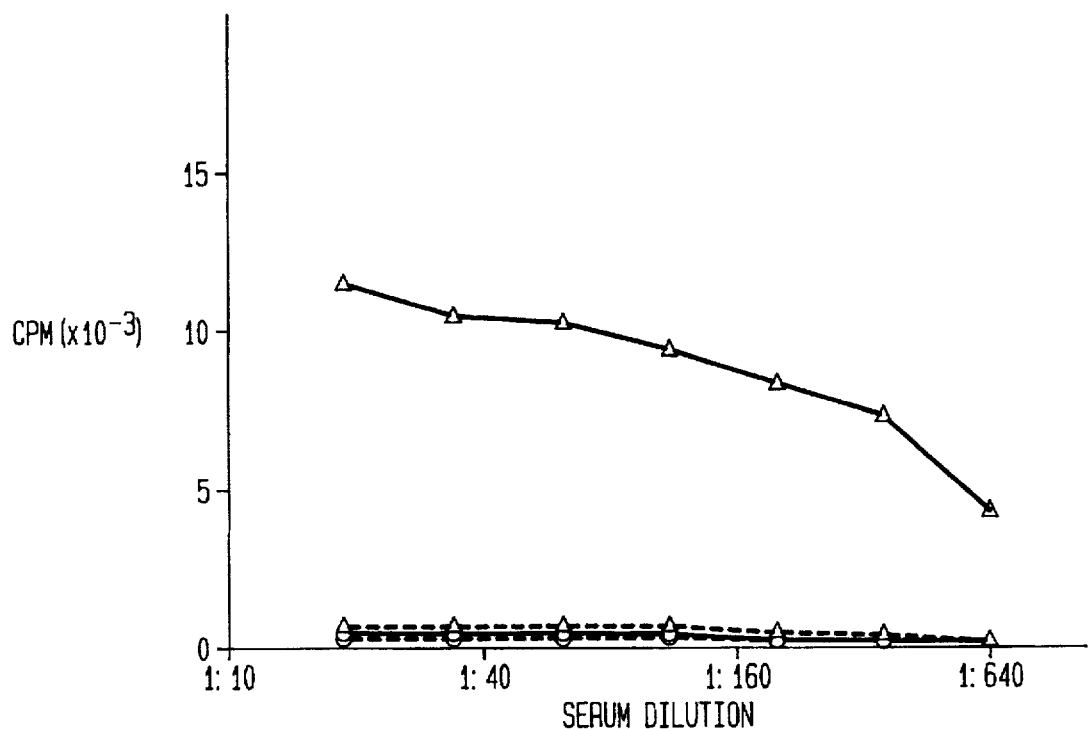

FIG. 2: Reactivity of anti-antiidiotypic MAb MK2-23 serum (from a Balb/c mouse) with cultured melanoma cells Symbols:

straight line: melanoma cells Colo 38 dotted line: B lymphoid cells LG-2 (control)

triangles: immune serum circles: preimmune serum (control)

EXAMPLES

Example 1

Preparation of Hybridoma Cell Lines Secreting Antiidiotypic Monoclonal Antibodies to Anti-HMW-MAA MAb 763.74

1.1 Immunization protocol

Eight to twelve weeks old male Balb/c mice (Charles River Breeding Laboratory, Wilmington, Mass., USA) each receive an intraperitoneal (i.p.) injection of 200 µg purified anti-HMW-MAA MAb 763.74 (P. Giacomini et al., J. Immunol. 135, 696, 1985) which is coupled to keyhole limpet haemocyanin (KLH) (Sigma), polymerized with 4 µl of a 2.5% solution of glutaraldehyde in PBS pH 7.2 and mixed with an equal volume of complete Freund's adjuvant (CFA) (Gibco). The coupling and polymerization procedure is carried out according to G. Buttin et al. (Curr. Top. Microbiol. 81, 27, 19878). The mice are then boosted i.p. with 200 µg of the same immunogen in incomplete Freund's adjuvant (IFA) on day 7. The second booster with an intraperitoneal injection of 200 µg of the same immunogen in PBS pH 7.3, is given on day 30. Three days after the second booster injection, the mice are sacrificed, the spleen is removed and splenocytes are fused with the murine myeloma cells P3-X63-Ag8.653 as described in example 1.2.

1.2 Cell fusion

Cell fusion is accomplished using $10^8$ spleen cells of the immunized mice and $3 \times 10^9$ cells from the mouse myeloma cell line P3-X63-Ag8.653 in the presence of 1 ml of 50% polyethylene glycol (PEG 4000, Merck) according to conventional previously described methods (Köhler and Milstein, Nature 256, 495, 1975). After washing, the cells are resuspended in 300 ml of Standard Dulbecco's Minimum Essential Medium (Seromed), 15% fetal calf serum and $3 \times 10^6$ normal mouse peritoneal exudate cells are added per fusion as feeder cells. The cells are distributed between six 48×1 ml Costar plates. The cultures are fed twice weekly with HAT selective medium, later with HT medium, for 3 to 6 weeks. The hybridomas are screened with the assay described in example 1.3.

1.3 Screening of hybridoma supernatants for the presence of antiidiotypic MAbs

The hybridoma supernatants are tested for the presence of antiidiotypic MAbs in a binding assay with F(ab')$_2$ fragments of monoclonal antibodies and a sandwich immunoassay.

For the indirect binding assay, F(ab')$_2$ fragments of MAb 763.74 are prepared as described by Kusama et al. (Cancer Res. 4, 4312, 1987). 96-well polyvinylchloride microtiter plates (Dynatech) are coated with the F(ab')$_2$ fragments of MAb 763.74 by adding to each well 50 µl of antibody fragment solution (5 µg/ml) in 0.1M bicarbonate buffer pH 9.5. After 16 hrs of incubation at 4° C., the plates are washed twice with PBS pH 7.4 supplemented with 0.05% Tween 20. 50 µl/well of hybridoma supernatants are added After 6 hrs incubation at 4° C., the plates are washed four times with PBS-T20, and $^{125}$I-labelled anti-mouse IgG xenoantibodies (Jackson Immunoresearch Lab; 1×10$^5$ cpm) are added. After 4 hrs incubation at 4° C., the plates are washed four times with PBS-T20, and bound radioactivity is measured in a gamma counter.

For the sandwich immunoassay, 96-well microtiter plates (Dynatech) are coated with MAb 763.74 by incubating 100 µl of monoclonal antibody solution (100 µg/ml) in 0.1M bicarbonate buffer pH 9.5 for 16 hrs at 4° C. Following three washings with PBS pH 7.4 supplemented with 0.05% Tween 20, 100 µl of hybridoma supernatants are added and incubation is continued for 4 hrs at $_4$° C. The plates are washed three times with PBS-T20 and incubated for 4 hrs at 4° C. with $^{125}$I-labelled MAb 763.74 (1×10$^5$ cpm). Following five washings with PBS-T20, bound radioactivity is counted in a gamma counter.

Hybridomas producing antiidiotypic antibodies are detected at a frequency of 4.9%.

The hybridoma supernatants are also tested with HMW-MAA carrying human melanoma cells Colo 38 (Quinn et al., J. Natl. Cancer Inst. 59, 301, 1977) in a binding assay similar to the binding assay described above using the cells as targets instead of the antibody F(ab')$_2$ fragments. 1.2% of the hybridoma supernatants are found to be positive in this test. All these hybridomas are different from those secreting antiidiotypic MAbs. Additional testing of these supernatants shows that they also react with human lymphoid cells LG-2 (R. A. Gatti & W. Leibod, Tissue Antigens 13, 35, 1979). These antibodies are likely to be secreted by hybridomas generated with splenocytes producing natural antibodies to human nucleated cells.

Of the hybridomas secreting antiidiotypic monoclonal antibodies, three are designated MK2-23, MK2-72 and MK2-120, respectively. They secrete the antiidiotypic monoclonal antibodies with the designation MAb MK2-23, MAb MK2-72 and MK2-120, respectively.

Example 2

Production, Isolation and Purification of MAb MK2-23

2.1 Expansion of hybridomas in vivo and purification of monoclonal antibodies

For ascites production, female Balb/c mice (20–25 g) are pretreated with 0.3 ml pristane oil (Aldrich) i.p. One to three weeks later, the mice receive a second injection of pristane (0.2 ml i.p.) and are simultaneously inoculated i.p. with 2×10$^6$ hybridoma cells in 0.2 ml PBS. After eight to ten days, the resulting ascites fluid is collected, centrifugated at 800 g and stored at −20° C. or at −80° C.

The monoclonal antibodies are purified from ascitic fluid by a two step procedure. Following caprylic acid or 40% ammonium sulphate precipitation, the antibodies are purified by ion exchange chromatography on DEAE.

Purity is assessed by sodium dodecylsulphate-polyacrylamide gel electrophoresis (SDS-PAGE).

2.2 Expansion of hybridomas in vitro

Precultures of the hybridoma cells are obtained by culturing hybridoma cells at physiological temperature (around 37° C.) in RPMI 1640 medium (Seromed) containing 10% FCS to a final cell density of 5×10$^5$ to 10$^6$ cells. The whole preculture is filled into Bellco culture vessels and adjusted to a total volume of 1500 ml with fresh RPMI 1640 medium/ 10% FCS and stirred for another seven to ten days. After this time, 95% of the cells are dead. The culture broth is centrifuged at 1000 g for 20 min at 4° C. The supernatant is filtered through a filter with pore size 0.2 µm under sterile conditions. Crude immunoglobulin is precipitated by slow dropwise addition of 0.9 volume equivalents of saturated ammonium sulphate at 0° C. This precipitate is purified as described in example 2.1.

Example 3

Characterization of the Antiidiotypic MAb MK2-23

MAb MK2-23 is further characterized in the following.

3.1 Specificity

MAb MK2-23 is radiolabelled with $^{125}$I utilizing the chloramine T method and tested in a binding assay with a panel of reference MAbs directed against HMW-MAA, HLA Class I antigens and HLA Class II antigens. The specificities of the reference antibodies are given in Table 2 below.

The test is carried out as follows. Microtiter plates (Dynatech) coated with the reference monoclonal antibodies are incubated for 4 hrs at 4° C. with $^{125}$I-labelled antiidiotypic MAbs (2×10$^5$ cpm/well). Then the plates are washed with PBS-T20, and bound radioactivity is measured in a gamma-counter. As shown by the results given in Table 2 below, MK2-23 only reacts with the immunizing MAb 763.74.

TABLE 2

Specificity of MAb MK2-23

| reference MAb | Ig class | specificity | source | MAb MK2-23* |
|---|---|---|---|---|
| 149.53 | G1 | HMW-MAA | 1 | 0.6 |
| 653.25 | G1 | HMW-MAA | 2 | 0.8 |
| 763.74 | G1 | HMW-MAA | 1 | 23.3 |
| 657.5 | G1 | HMW-MAA | 3 | 0.7 |
| 902.51 | G1 | HMW-MAA | 3 | 0.6 |
| 225.28 | G2a | HMW-MAA | 1 | 0.5 |
| CR11-351 | G1 | HLA-A2,A28 | 4 | 0.8 |
| KS1 | G1 | HLA-A2,A28 | 5 | 0.7 |
| KS3 | G2b | HLA-B7, cross-reacting group | 6 | 0.6 |
| Q6/64 | G2a | HLA-B | 7 | 0.7 |
| CR10-215 | G1 | HLA-Class I | 8 | 0.7 |
| Q1/28 | G1 | HLA-Class I | 9 | 0.7 |
| CR11-115 | G2b | HLA-Class I | 8 | 0.8 |
| NAMB-1 | G1 | β$_2$-microglobulin | 10 | 0.6 |
| AC1.59 | M | HLA-DR1,4, w6,w8,w9 | 11 | 0.3 |
| B7/21 | G2a | HLA-DP | 12 | 0.3 |
| Q2/70 | G1 | HLA-DR | 13 | 0.4 |
| CR11-462 | G1 | HLA-DP,DR | 4 | 0.5 |
| Q5/13 | G2a | HLA-DP,DQ,DR | 13 | 0.7 |

Legend:
*$^{125}$I-labelled MAb MK2-23 (cpm × 10$^{-3}$)
1 P. Giacomini et al.; J. Immunol. 135, 696 (1985)
2 K. Imai et al., Cell. Immunol. 72, 239 (1982)
3 M. R. Ziai et al., Cancer Res. 47, 2474 (1987)
4 C. Russo et al., Immunogenetics 18, 23 (1983)
5 M. Tsujisaki et al., Transplantation 445, 632 (1988)
6 K. Sakaguchi et al., Hum. Immunol. 21, 193 (1988)
7 V. Quaranta et al., Immunogenetics 14, 403 (1981)
8 M. C. Turco et al., J. Immunol. 135, 2268 (1985)
9 V. Quaranta et al., Immunogenetics 13, 285 (1981)
10 M. A. Pellegrino et al., Transplantation 34, 18 (1982)
11 T. Crepaldi et al., Tissue Antigens 26, 25 (1985)
12 A. J. Watson et al., Mol. Immunol. 19, 755 (1982)
13 V. Quaranta et al., J. Immunol. 126, 548 (1981)

3.2 Inhibition of the binding of the immunizing anti-HMW-MAA MAb 763.74 to melanoma cells To investigate the relationship between the idiotopes defined by the antiidiotypic monoclonal antibody MK2-23 and the antigen combining site of the immunizing anti-HMW-MAA MAb 763.74. MAb MK2-23 is tested for its ability to inhibit the binding of MAb 763.74 to cultured melanoma cells Colo 38.

$^{125}$I-labelled anti-HMW-MAA monoclonal antibody MAb 763.74 ($2\times10^5$ cpm/50 μl) is mixed with 50 μl of a solution of purified unlabelled antiidiotypic MAb MK2-23, MAb MK2-72 and MAb MK2-120. Following a 4 hrs incubation at 4° C., each mixture is added to cultured melanoma cells Colo 39 ($2\times10^5$). Incubation is continued for an additional 2 hrs at 4° C. The cells are washed five times with PBS, and bound radioactivity is counted in a gamma counter.

Figure 1:
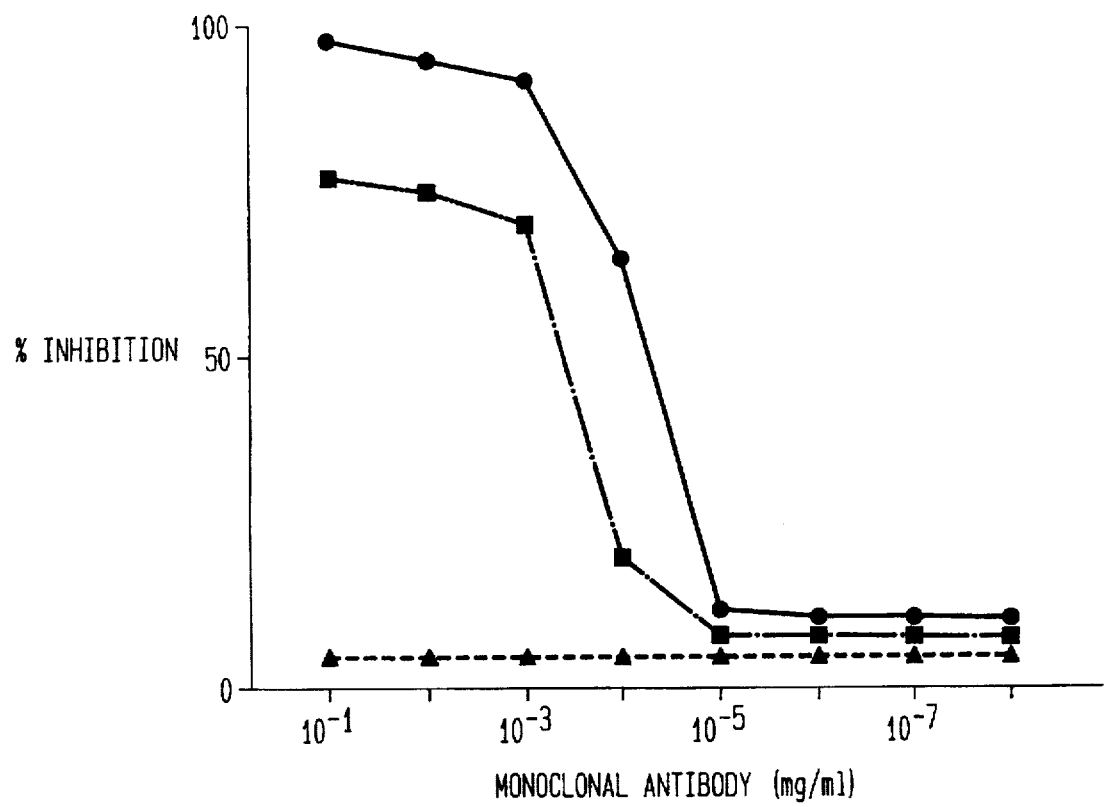
FIG. 1: Inhibition of the binding of $^{125}$I-labelled anti-HMW-MAA MAb 763.74 to cultured melanoma cells Colo 38 by antiidiotypic MAbs Symbols.

The results are shown in FIG. 1. The inhibition is specific since MAb MK2-23 does not affect the binding of a monoclonal antibody directed against distinct determinants of HMW-MAA to the melanoma cells. Furthermore, the binding of anti-HMW-MAA monoclonal antibody 763.74 to melanoma cells is not affected by an irrelevant antiidiotypic MAb.

3.3 Mapping of idiotopes

Crossblocking experiments are performed with a selected number of antiidiotypic MAbs to map the idiotopes recognized by MAb MK2-23 on the immunizing anti-HMW-MAA MAb 763.74.

To this end, microtiter plates are coated with the monoclonal antibody MAb 763.74 as described before. After incubation for 4 hrs at 4° C. with twofold dilutions of unlabelled antiidiotypic antibodies MAb MK2-23, MAb MK2-72 and MAb2-120, respectively (final concentration ranging between 100 and 0.0001 μg/ml), plates are incubated for 4 hrs at 4° C. with each of the three antiidiotypic $^{125}$I-labelled MAbs ($2\times10^5$ cpm) in PBS pH 7.4. Then the plates are washed with PBS supplemented with Tween 20, and bound radio-activity is measured in a gamma counter.

The results are shown in Table 3 below.

TABLE 3

| | Idiotopes recognized by antiidiotypic MAbs directed against MAb 763.74 | | |
|---|---|---|---|
| un-labelled | $^{125}$I-labelled antiidiotypic MAbs (% inhibition) | | |
| MAb | MK2-23 | MK2-72 | MK2-120 |
| MK2-23 | 92 | 88 | 0 |
| MK2-72 | 84 | 96 | 1 |
| MK2-120 | 2 | 1 | 80 |

Among the three antiidiotypic MAbs directed against MAb 763.74, MAb MK2-23 and MK2-72 crossinhibit each other, but do not inhibit and are not inhibited by MAb MK2-120. Therefore, MAb MK2-23 and MK2-72 recognize the same or spatially close idiotope(s) which are spatially distinct from the idiotope recognized by MAb MK2-120.

Example 4

Characteristics of Anti-Antiidiotypic Antibodies Elicited with MAb MK2-23

MAb MK2-23 can induce humoral and cell mediated immunity to HMW-MAA as shown by the following line of evidence (see also example 5). The following experiments also show that MAb MK2-23 is an internal image of HMW-MAA.

4.1 Preparation of anti-antiidiotypic antisera

Four Balb/c mice are primed with a subcutaneous injection of 50 μg of antiidiotypic MAb MK2-23 coupled to KLH, polymerized with glutaraldehyde and mixed with CFA (see example 1.1). The mice are then boosted with 50 μg of the same immunogen in IFA on day 14 and in PBS on day 28. Serum is harvested on day 42. A control group of mice is treated in the same way with antiidiotypic MAb MK2-120 directed against idiotopes outside the antigen combining sites of the immunizing monoclonal antibody MAb 763.74.

4.2 Binding of the anti-antiidiotypic antibodies to melanoma cells

Serum from each mouse is tested for its reactivity with cultured melanoma cells Colo 38 and with cultured B lymphoid cells LG-2. 50 μl of immune and preimmune sera are added to $2\times10^5$ melanoma and lymphoid cells, respectively. After incubation for 2 hrs at 4° C., the cells are washed, and $^{125}$I-labelled anti-mouse Ig xenoantibodies ($1\times10^5$ cpm) are added Incubation is prolonged for an additional 2 hrs. Then the cells are washed five times with PBS, and bound radioactivity is measured in a gamma counter.

Only sera from mice immunized with the antiidiotypic monoclonal antibody MAb MK2-23 react with the melanoma cells Colo 38, as shown in FIG. 2. The binding is specific since the immune serum does not react with cultured B lymphoid cells LG-2 (see also FIG. 2).

4.3 Specificity of the anti-antiidiotypic antibodies elicited with MAb MK2-23

To prove that the antibodies elicited with MAb MK2-23 react with HMW-MAA, i.e. are anti-HMW-MAA antibodies, SDS-PAGE analysis of the antigens immunoprecipitated from cultured melanoma cells Colo 38 by serum from Balb/c mice immunized with MAb MK2-23 is carried out.

To this end, cultured melanoma cells Colo 38 are labelled with $^{125}$I using the lactoperoxidase method and solubilized with NP 40. After indirect immunoprecipitation with anti-MAb MK2-23 serum, antigens are eluted from the immunoadsorbent and analyzed by SDS-PAGE in 5% slab gels in the presence of 2% β-mercaptoethanol. Solubilization with NP 40, immunoprecipitation and SDS-PAGE are performed as described by Wilson et al. (Int. J. Cancer 28, 293, 1981). MAb 763.74 and normal mouse serum are used as controls. Gels are processed for autoradiography using a Kodak XAR-5 film (Eastman Kodak Co.).

The SDS-PAGE analysis shows that the anti-MAb MK2-23 serum contains antibodies reacting with HMW-MAA, since the anti-MAb MK2-23 immunoprecipitates components with the characteristic electrophoretic profile of HMW-MAA from the cultured melanoma cells Colo 38.

4.4 Reactivity of the anti-antiidiotypic antibodies with MAb MK2-23 and its fragments First, the binding ability of the anti-antiidiotypic antibodies to F(ab')$_2$ fragments of the syngeneic antiidiotypic MAb MK2-23 is tested.

F(ab')$_2$ fragments of MAb MK2-23 are generated following the procedure described by Parham (J. Immunol. 131, 2895, 1983). Briefly, purified MAb MK2-23 is incubated with pepsin (Sigma) in an enzyme:protein ratio of 1:40. Digestion is performed at 37° C. for 8 hrs at pH 3.5. The reaction is stopped by raising the pH to 7.0 with 1M Tris solution. Then the mixture is dialyzed against PBS pH 7.4, and concentrated. Fc fragments and undigested immunoglobulins are removed by affinity chromatography on Protein A-Sepharose.

The test for reactivity of the anti-antiidiotypic sera with the F(ab')$_2$ fragments of MAb MK2-23 is carried out in analogy to the binding assay of example 4.2. Serum from each mouse reacts with the fragment preparation. The titer of antibodies reactive with MAb MK2-23 F(ab')$_2$ fragments is markedly higher than that of antibodies reactive with cultured melanoma cells.

Furthermore, it is examined whether the anti-antiidiotypic sera inhibit the binding of $^{125}$I-labelled MAb MK2-23 to the immunizing anti-HMW-MAA MAb 763.74. As control, it is also tested whether the anti-antiidiotypic sera inhibit the binding of other antiidiotypic monoclonal antibodies to their corresponding immunizing anti-HMW-MAA MAbs which recognize determinants distinct from the one defined by MAb 763.74. The inhibition assay is performed by incubating 100 μl of the anti-antiidiotypic serum to be tested with the $^{125}$I-labelled antiidiotypic MAb ($2\times10^5$ cpm) for 4 hrs at 4° C. Then the mixture is added to the wells of microtiter plates coated with the immunizing monoclonal antibody (1 μg/well). After incubation for 2 hrs at room temperature, the plates are washed five times with PBS-T20. Bound radioactivity is measured in a gamma counter. Results are expressed as percentage of inhibition of the binding of the $^{125}$I-labelled antiidiotypic MAb in the presence of the anti-antiidiotypic serum as compared to binding performed in the presence of preimmune serum.

Sera from the mice immunized with the antiidiotypic MAb MK2-23 inhibit the binding of $^{125}$I-MAb MK2-23 to MAb 763.74. The dilution of serum giving 50% inhibition is much higher than that giving 50% of the maximal binding to cultured melanoma cells, but lower than giving 50% of the maximal binding to F(ab')$_2$ fragments of MAb MK2-23. The inhibitory activity of the sera is highly restricted, since they do not inhibit the binding of $^{125}$I-antiidiotypic MAb MF 11-30 to its immunizing MAb 225.28, of $^{125}$I-antiidiotypic MAb TK6-74 to its immunizing MAb TP41.2, and of $^{125}$I-antiidiotypic MAb TK7-110 to its immunizing MAb TP 61.5.

4.5 Immunoglobulin class of the anti-antiidiotypic antibodies

The immunoglobulin class of the anti-antiidiotypic antibodies which react with melanoma cells Colo 38 (see example 4.2) and of the anti-antiidiotypic antibodies which react with the F(ab')$_2$ fragments of MAb MK2-23 (see example 4.4) is determined in a modification of the the binding assay of example 4.2, using with $^{125}$I-labelled xenoantibodies specific for murine IgM and for murine IgG. In the group of antibodies reactive with MAb MK2-23 F(ab')$_2$ fragments, the large majority of the antibody population is of the IgG class, whereas the IgM component in the antibody group reactive with Colo 38 cells is only slightly lower than the IgG component.

4.6 Inhibition of the binding of the anti-antiidiotypic antibodies to melanoma cells by MAb MK2-23

Inhibition experiments are performed to determine whether the anti-antiidiotypic antibodies elicited with MAb MK2-23 express the corresponding idiotype in their antigen combining site.

The inhibition assay is performed by incubating anti-antiidiotypic serum (100 μl) with MAb MK2-23 for 2 hrs at RT. Then the mixture is added to cultured human melanoma cells Colo 38, and the incubation is continued for an additional 2 hrs at 4° C. Then the cells are washed three times with PBS-BSA and incubated with $^{125}$I-labelled anti-human Ig xenoantibodies. Following five additional washings, bound radioactivity is measured in a gamma counter. Results are expressed as percentage of inhibition as compared to binding in the presence of an unrelated antiidiotypic monoclonal antibody.

The anti-MAb MK2-23 serum displays decreased reactivity with cultured melanoma cells Colo 38 following incubation with MAb MK2-23. The inhibition is dose dependent. Furthermore, the inhibition is specific, since the antiidiotypic MAb TK6-74 elicited with the anti-HMW-MAA MAb TP41.2 does not affect the reactivity of the anti-MAb MK2-23 sera with cultured melanoma cells Colo 38. The results show clearly, that, like MAb 763.74, the anti-antiidiotypic antibodies express in their antigen binding site the idiotope recognized by MAb MK2-23.

4.7 Inhibition of the binding of anti-HMW-MAA MAb 763.74 to melanoma cells by the anti-antiidiotypic antibodies Crossinhibition experiments are performed to compare the fine specificity of the anti-antiidiotypic antibodies elicited by MAb MK2-23 with that of the anti-HMW-MAA MAb 763.74. The assay is carried out by incubating cultured melanoma cells Colo 38 ($2\times10^5$) with 100 μl of anti-antiidiotypic serum for 2 hrs at 4° C. Then the supernatant is removed, and $^{125}$I-labelled anti-HMW-MAA MAb 763.74 ($2\times10^5$ cpm) or $^{125}$I-labelled anti-ICAM-1 MAb CL207.14 are added to the cells. After incubation for 2 hrs at 4° C., the cells are washed five times with PBS-BSA, and bound reactivity is measured in a gamma counter. Results are expressed as percentage of inhibition of the binding of the radiolabelled monoclonal antibodies to cells preincubated with the anti-antiidiotypic serum as compared to the binding of the radiolabelled monoclonal antibodies to cells preincubated with preimmune sera.

Incubation of cultured melanoma cells Colo 38 with increasing dilution of anti-MAb MK2-23 serum inhibits the binding of $^{125}$I-labelled MAB 763.74 to Colo 38 cells in a dose dependent fashion. The maximal inhibition obtained with the lowest dilution of anti-antiidiotypic antiserum is about 60%. The inhibition is specific since incubation of culutred melanoma cells Colo 38 with anti-antiidiotypic serum does not affect the ability to bind $^{125}$I-labelled anti-ICAM-1 MAb CL207.14 and $^{125}$I-labelled anti-HMW-MAA MAb 225.28, which recognizes a distinct and spatially distant determinant of HMW-MAA from that recognized by MAb 763.74. On the other hand, the anti-antiidiotypic serum inhibits the binding to Colo 38 cells of $^{125}$I-labelled MAb VT80 which recognizes the same or a spatially close determinant of HMW-MAA as MAb 763.74 and crossinhibits the binding of MAb 763.74 to melanoma cells Colo 38. Furthermore, incubation with normal mouse serum does not affect the ability of Colo 38 cells to bind $^{125}$I-labelled MAb 763.74.

Example 5

Induction of Delayed Type Hypersensitivity by the Anti-Idiotypic MAb MK2-23

To determine whether immunization with antiidiotypic MAb MK2-23 induces delayed type hypersensitivity (DTH) against cultured human melanoma cells, Balb/c mice are immunized with MAb MK2-23 (see example 4.1) on day 0, 14 and 28 and then injected with $5\times10^5$ irradiated (20,000 Rad) cultured melanoma cells Colo 38 into the right hind foot pads on day 50. The thickness of swelling of each foot pad is measured at time 0 and after 24, 48 and 72 hrs with a Digit Outside Micrometer (Mitutoyo Corp.). Parallel injections of cultured B lymphoid cells LG-2 into the contralateral foot pads are carried out as controls.

A marked increase in the thickness of swelling is observed 24 hrs following the injection and persists 72 hrs following the rechallenge. The increase is significantly higher than that observed with in the food pads injected with the LG-2 cells.

Example 6

Factors Influencing the Immunogenicity of the Antiidiotypic MAb MK2-23

6.1 Effect of the dose of MAb MK2-23

To investigate the effect of the dose of MAb MK2-23 on the induction of anti-antiidiotypic antibodies, three groups of four mice each are injected with 5 µg (group A), with 50 µg (group B) and with 500 µg (group C) of MAb MK2-21 (conjugated to KLH and mixed with CFA on day 0, with IFA on day 14 and PBS on day 28). Serum is harvested on day 42 and tested with cultured melanoma cells Colo 38 and with F(ab')$_2$ fragments of MAb MK2-23 in binding assays with $^{125}$I-labelled anti-mouse Ig xenoantibodies. The test procedures are carried out in analogy to the assays described in examples 4.2 and 4.3. Antibodies reacting with Colo 38 cells are detected in the sera of one group A-mouse, in all group B-mice, and in two group C-mice. None of the sera displays reactivity with cultured B lymphoid cells LG-2. All the mice develop anti-antiidiotypic antibodies reacting with F(ab')$_2$ fragments of MAb MK2-23. Irrespective of the dose of MAb MK2-23 used for immunization, the level of the antibodies reacting with cultured melanoma cells Colo 38 is lower than that of those reacting with F(ab')$_2$ fragments of MAb MK2-23. Furthermore, the level of the latter antibodies is relatively lower in mice injected with 5 µg of MAb MK2-23 than in those injected with 50 and 500 µg, but is similar in the latter two groups.

6.2 Effect of the number of immunizations with MAb MK2-23

To investigate the effect of the number of immunizations on the induction of anti-antiidiotypic antibodies, three groups of four mice each are primed with 50 µg of MAb MK2-23 conjugated with KLH and mixed with CFA on day 0 and then treated further according to different schedules:

group A: no additional immunization, group B: booster immunization with MAb MK2-23 conjugated with KLH and mixed with IFA on day 14;

group C: booster immunizations on day 14 and 28 with MAb MK2-23 conjugated with KLH and mixed with IFA on day 14 and with PBS on day 28.

Sera are harvested on day 42 and tested for reactivity with cultured melanoma cells Colo 38 and with F(ab')$_2$ fragments of MAb MK2-23 in binding assays with $^{125}$I-labelled anti-mouse Ig xenoantibodies. Antibodies reacting with cultured melanoma cells Colo 38 are detected in one group A-mouse, in all group B-mice and in three group C-mice. None of the sera displays reactivity with cultured B lymphoid cells LG-2. All the mice induce anti-antiidiotypic antibodies reacting with F(ab')$_2$ fragments of MAb MK2-23. The level of the latter antibodies is lower in mice injected only once than in the other two groups of mice between which no marked difference is found. Irrespective of the number of immunizations, antibodies reacting with F(ab')$_2$ fragments of MAb MK2-23 display a relatively higher level or are even present in mice without detectable antibodies reacting with Colo 38 cells.

6.3 Effect of carrier and adjuvant

To investigate the effect of conjugation to a carrier and/or of adjuvants on the immunogenicity of MAb MK2-23, groups of four mice each are immunized on day 0 and 14 with 50 µg of antibody presented in the following way:

group A: unconjugated MAb MK2-23 group B: MAb MK2-23 conjugated with KLH, group C: MAb MK2-23 mixed with CFA for priming and with IFA for boosting.

Serum is harvested on day 42 and tested for reactivity with cultured melanoma cells Colo 38 and with F(ab')$_2$ fragments of MAb MK2-23.

The serum from one mouse immunized with MAD MK2-23 mixed with adjuvant (group C) displays a low reactivity with cultured melanoma cells Colo 38, whereas no antibodies reacting with Colo 38 cells are detected in the sera of the remaining mice. The sera from the mice injected with unconjugated MAb MK2-23 (group A) do not react with F(ab')$_2$ fragments of MAb MK2-23, while sera from all the mice in the other two groups display a similar low binding activity and inhibit the binding of $^{125}$I-labelled MAb MK2-23 to MAb 763.74 by less than 50%.

Example 7

Pharmaceutical Composition

0.25 mg antiidiotypic monoclonal antibody MAb MK2-23 prepared according to examples 1 and 2 are dissolved in 5 ml physiological saline. The solution is passed through a bacteriological filter, and the filtrate filled in an ampoule under aseptic conditions. The ampoule is preferentially stored in the cold, e.g. at −20° C.

Example 8

Therapeutic Application of the Antiidiotypic Monoclonal Antibody MAb MK2-23

The antiidiotypic monoclonal antibody MK2-23 is utilized in a clinical trial with patients suffering from advanced (stage IV) melanoma. The patients have been treated before unsuccessfully with various types of therapy, including biological response modifiers.

Fifteen patients are immunized with 2 mg of MAb MK2-23 conjugated to KLH and mixed with Bacillus Calmette-Guerin (BCG), and 12 patients are immunized with MAb MK2-23 (without conjugation and adjuvant). Immunizations are administered intradermally on day 0, 7 and 28. Sera are obtained every week and tested for development of anti-antiidiotypic antibodies (antibodies which inhibit the binding of the antiidiotypic antibody used as immunogen to the corresponding anti-HMW-MAA antibody), reactivity with HMW-MAA bearing melanoma cells, the HMW-MAA level and the development of anti-mouse antibodies. An escalation dose trial shows that the 2 mg dose per injection is more effective than lower doses and as effective as higher doses in inducing anti-antiidiotypic antibodies.

Antibodies reacting with melanoma cells Colo 38 are detected in 73% of the patients immunized with MAb MK2-23 coupled to KLH and mixed with BCG and in 16% of the patients immunized with unconjugated MAb MK2-23. These results show that, in agreement with the data obtained in animal model systems (see example 6.3), conjugation of the monoclonal antibody to a carrier molecule and mixing with an adjuvant enhances its immunogenicity.

Sera from the immunized patients inhibit partially the binding of $^{125}$I-labelled anti-HMW-MAA MAb 763.74 to Colo 38 melanoma cells in a specific fashion. MAb MK2-23 inhibits the binding of sera from the immunized patients to cultured melanoma cells Colo 38.

Anti-murine Ig antibodies are removed from patients' sera and the antibodies induced by MK2-23 in the sera are purified by affinity chromatography on insolubilized MAb MK2-23. The purified antibodies react with HMW-MAA which is isolated from an extract of melanoma cells Colo 38 by affinity chromatographgy on insolubilized anti-HMW-MAA MAb 149.53.

About 85% of the patients immunized with MAb MK2-23 conjugated to KLH and mixed with BCG and about 60% of the patients treated with uncoupled MAb MK2-23 develop anti-antiidiotypic antibodies which inhibit the binding of $^{125}$I-labelled MK2-23 to the anti-HMW-MAA MAb 763.74.

Almost all patients develop increased levels of anti-mouse Ig antibodies, without a marked difference between the two groups of patients.

Reduction in the size of metastatic lesions is observed in at least six of the immunized patients.

The data indicate that the murine antiidiotypic MAb MK2-23 induces anti-HMW-MAA antibodies in patients which express HMW-MAA in their melanoma lesions but show no detectable anti-HMW-MAA immune response. Therefore, the antiidiotypic MAb MK2-23 appears to be more immunogenic than the corresponding antigen HMW-MAA itself.

I claim:

1. A pharmaceutical composition for the treatment of melanoma comprising a murine antiidiotypic monoclonal antibody designated Mab MK2-23 which is produced by the hybridoma cell line deposited with the American Type Culture Collection (ATCC) under accession No. HB 10288 or a conjugate or fragment thereof retaining the specificity of antibody MK2-23 and a pharmaceutically acceptable carrier.

2. A pharmaceutical composition according to claim 1 wherein antibody MK2-23, or a fragment thereof that retains the specificity of antibody MK2-23, is conjugated with a carrier which enhances immunogenicity thereof.

3. A pharmaceutical composition according to claim 2 wherein the carrier is keyhole limpet haemocyanin (KLH).

4. A pharmaceutical composition according to claim 3 further comprising the adjuvant Bacillus Calmette-Guerin (BCG).

5. A method of treating a warm-blooded animal including man in need of treatment of melanoma which comprises administering to said animal a therapeutically effective amount of a murine antiidiotypic monoclonal antibody designated Mab MK2-23 which is produced by the hybridoma cell line deposited with the American Type Culture Collection (ATCC) under accession No. HB 10288 or a conjugate or fragment thereof retaining the specificity of antibody MK2-23.

6. A method of treating a warm-blooded animal including man in need of treatment of melanoma which comprises administering to said animal a therapeutically effective amount of a conjugate or fragment of a murine antiidiotypic monoclonal antibody designated Mab MK2-23 which is produced by the hybridoma cell line deposited with the American Type Culture Collection (ATCC) under accession No. HB 10288 which conjugate or fragment retains the specificity of antibody MK2-23.

* * * * *

UNITED STATES PATENT AND TRADEMARK OFFICE
CERTIFICATE OF CORRECTION

PATENT NO. : 5,780,029
DATED : July 14, 1998
INVENTOR(S) : Soldano Ferrone

It is certified that error appears in the above-identified patent and that said Letters Patent is hereby corrected as shown below:

TITLE PAGE:
In the caption, item [54], "Antidiotypic" should read "Antiidiotypic."

In column 1, line 1 (in the title), "Antidiotypic" should read "Antiidiotypic."

Signed and Sealed this

Twenty-seventh Day of October, 1998

Attest:

BRUCE LEHMAN

Attesting Officer          Commissioner of Patents and Trademarks